(12) United States Patent
Baril et al.

(10) Patent No.: US 11,864,818 B2
(45) Date of Patent: Jan. 9, 2024

(54) END EFFECTOR ASSEMBLY FOR BIPOLAR PENCIL

(71) Applicant: Covidien LP, Mansfield, MA (US)

(72) Inventors: Jacob C. Baril, Norwalk, CT (US); Saumya Banerjee, Hamden, CT (US); Ernest A. Addi, Middletown, CT (US); Amy L. Kung, Hamden, CT (US); Brian J. Creston, Madison, CT (US); Scott J. Prior, Shelton, CT (US); Thomas A. Zammataro, North Haven, CT (US); Christopher M. Meehan, New Haven, CT (US); Matthew A. Dinino, Newington, CT (US); Justin J. Thomas, New Haven, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 782 days.

(21) Appl. No.: 16/900,293

(22) Filed: Jun. 12, 2020

(65) Prior Publication Data

US 2021/0386473 A1  Dec. 16, 2021

(51) Int. Cl.
*A61B 18/14* (2006.01)
*A61B 18/12* (2006.01)
(Continued)

(52) U.S. Cl.
CPC ...... *A61B 18/1402* (2013.01); *A61B 18/1206* (2013.01); *A61B 18/16* (2013.01);
(Continued)

(58) Field of Classification Search
CPC ...... A61B 2018/1407; A61B 2018/144; A61B 18/149; A61B 18/1402; A61B 18/1206;
(Continued)

(56) References Cited

U.S. PATENT DOCUMENTS 2,022,065 A  11/1935  Wappler
2,047,535 A  7/1936  Wappler
(Continued)

FOREIGN PATENT DOCUMENTS

WO  2016025132 A1  2/2016

*Primary Examiner* — Sean W Collins
(74) *Attorney, Agent, or Firm* — Carter, DeLuca & Farrell LLP

(57) ABSTRACT

An electrode assembly for an electrosurgical instrument includes a housing having an active electrical connector and a return electrical connector configured to operably engage a distal end of an electrosurgical instrument shaft, the housing encapsulating an elongated return electrode and a pair of insulative tubes configured to house a wire-like active electrode. The elongated return electrode includes a clevis at a distal end thereof and operably engages to the return electrical connector at a proximal end thereof. The wire-like active electrode operably engages at one end to the active electrical connector. A donut-like insulator is operably engaged to the clevis of the elongated return electrode and is configured to support the wire-like active electrode therearound. A tensioning mechanism is configured to operably engage an opposite end of the wire-like electrode and tension the wire-like active electrode about the donut-like insulator during assembly.

20 Claims, 12 Drawing Sheets

(51) Int. Cl.
    *A61B 18/16* (2006.01)
    *A61B 18/00* (2006.01)
    *A61B 17/00* (2006.01)

(52) U.S. Cl.
    CPC ..... *A61B 18/149* (2013.01); *A61B 2017/0088* (2013.01); *A61B 2017/00367* (2013.01); *A61B 2017/00734* (2013.01); *A61B 2018/00077* (2013.01); *A61B 2018/00178* (2013.01); *A61B 2018/00589* (2013.01); *A61B 2018/00595* (2013.01); *A61B 2018/00601* (2013.01); *A61B 2018/00684* (2013.01); *A61B 2018/00946* (2013.01); *A61B 2018/126* (2013.01); *A61B 2018/1253* (2013.01); *A61B 2018/144* (2013.01); *A61B 2018/1407* (2013.01); *A61B 2018/1412* (2013.01); *A61B 2018/1495* (2013.01)

(58) Field of Classification Search
    CPC .......... A61B 18/16; A61B 2017/00367; A61B 2018/00178; A61B 2018/00946
    See application file for complete search history.

(56) References Cited

U.S. PATENT DOCUMENTS

| | | | |
|---|---|---|---|
| 3,516,412 A | 6/1970 | Ackerman | |
| 3,886,944 A | 6/1975 | Jamshidi | |
| 4,161,950 A | 7/1979 | Doss et al. | |
| 4,196,734 A | 4/1980 | Harris | |
| 4,198,957 A | 4/1980 | Cage et al. | |
| 4,485,810 A | 12/1984 | Beard | |
| 4,534,347 A | 8/1985 | Taylor | |
| 4,622,966 A | 11/1986 | Beard | |
| 4,633,880 A | 1/1987 | Osypka et al. | |
| 4,862,890 A | 9/1989 | Stasz et al. | |
| 4,936,843 A * | 6/1990 | Sohngen | A61B 17/6441 606/56 |
| 5,013,312 A | 5/1991 | Parins et al. | |
| 5,085,659 A | 2/1992 | Rydell | |
| 5,300,068 A | 4/1994 | Rosar et al. | |
| 5,360,428 A | 11/1994 | Hutchinson, Jr. | |
| 5,441,499 A | 8/1995 | Fritzsch | |
| 5,531,744 A | 7/1996 | Nardella et al. | |
| 5,536,267 A | 7/1996 | Edwards et al. | |
| 5,599,295 A | 2/1997 | Rosen et al. | |
| 5,599,346 A | 2/1997 | Edwards et al. | |
| 5,611,798 A | 3/1997 | Eggers | |
| 6,027,501 A | 2/2000 | Goble et al. | |
| 6,217,528 B1 | 4/2001 | Koblish et al. | |
| 6,471,701 B2 * | 10/2002 | Brommersma | A61B 18/149 606/46 |
| 6,494,881 B1 | 12/2002 | Bales et al. | |
| 6,530,924 B1 * | 3/2003 | Ellman | A61B 18/149 606/49 |
| 6,533,781 B2 | 3/2003 | Heim et al. | |
| 6,752,767 B2 | 6/2004 | Turovskiy et al. | |
| 7,033,354 B2 | 4/2006 | Keppel | |
| 7,156,842 B2 | 1/2007 | Sartor et al. | |
| 7,371,234 B2 | 5/2008 | Young | |
| 7,399,299 B2 | 7/2008 | Daniel et al. | |
| 7,419,488 B2 | 9/2008 | Ciarrocca et al. | |
| 7,846,108 B2 | 12/2010 | Turovskiy et al. | |
| 7,846,158 B2 | 12/2010 | Podhajsky | |
| 8,137,345 B2 | 3/2012 | McNall, III et al. | |
| 8,968,301 B2 | 3/2015 | Weber | |
| 9,060,765 B2 | 6/2015 | Rencher et al. | |
| 9,358,065 B2 | 6/2016 | Ladtkow et al. | |
| 9,445,863 B2 | 9/2016 | Batchelor et al. | |
| 9,775,665 B2 | 10/2017 | Ellman | |
| 9,993,287 B2 | 6/2018 | Sartor et al. | |
| 10,045,761 B2 | 8/2018 | Weber | |
| 10,376,314 B2 | 8/2019 | van der Weide et al. | |
| 10,433,898 B2 | 10/2019 | Borgmeier et al. | |
| 10,433,899 B2 | 10/2019 | Borgmeier et al. | |
| 10,531,917 B2 | 1/2020 | Johnson et al. | |
| 2002/0049441 A1 * | 4/2002 | George | A61B 18/1485 600/564 |
| 2005/0065510 A1 * | 3/2005 | Carmel | A61B 18/148 606/41 |
| 2005/0070895 A1 | 3/2005 | Ryan et al. | |
| 2005/0283149 A1 * | 12/2005 | Thorne | A61B 18/1402 606/48 |
| 2007/0078454 A1 | 4/2007 | McPherson | |
| 2007/0118110 A1 | 5/2007 | Girard et al. | |
| 2007/0149966 A1 | 6/2007 | Dahla et al. | |
| 2007/0179494 A1 | 8/2007 | Faure | |
| 2007/0219546 A1 | 9/2007 | Mody et al. | |
| 2007/0260240 A1 | 11/2007 | Rusin | |
| 2007/0265609 A1 | 11/2007 | Thapliyal et al. | |
| 2008/0281323 A1 | 11/2008 | Burbank et al. | |
| 2009/0306642 A1 | 12/2009 | Vankov | |
| 2011/0009863 A1 * | 1/2011 | Marczyk | A61B 18/1445 606/51 |
| 2012/0116416 A1 | 5/2012 | Neff et al. | |
| 2019/0083172 A1 | 3/2019 | Ladtkow et al. | |

* cited by examiner

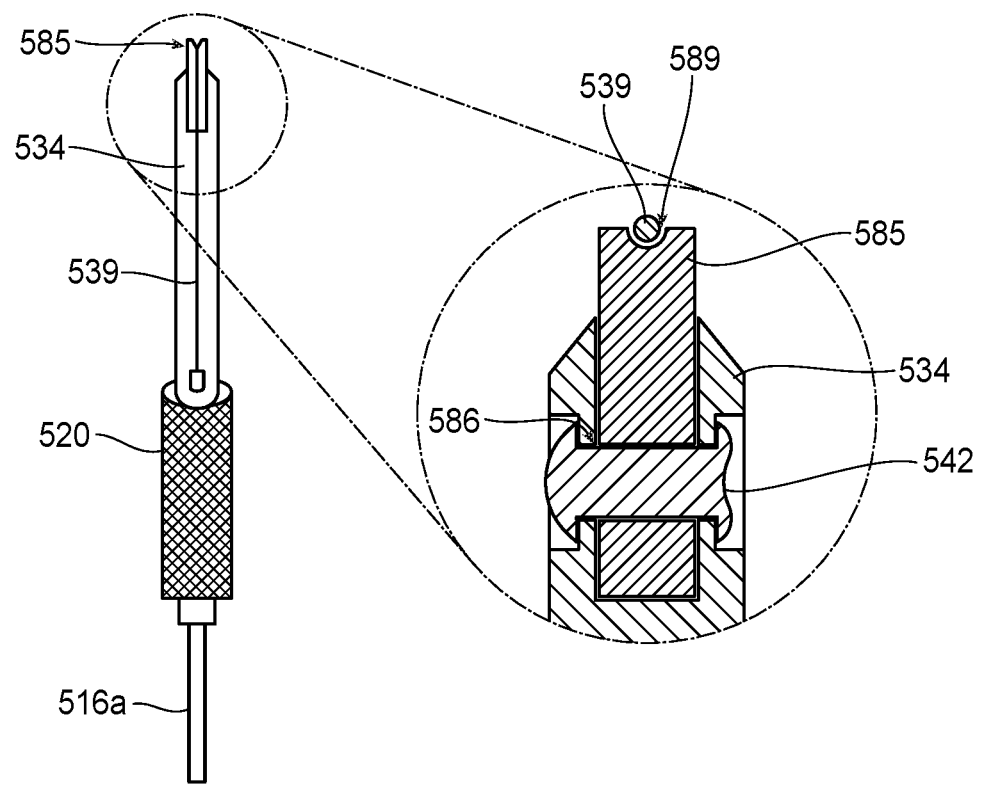
*Fig. 7C*  *Fig. 7D*

END EFFECTOR ASSEMBLY FOR BIPOLAR PENCIL

BACKGROUND

Technical Field

The present disclosure relates generally to electrosurgical instruments and, more particularly, to an electrosurgical bipolar pencil having a donut-style end effector assembly and a tensioning mechanism.

Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow pre-set control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is an electrode assembly for an electrosurgical instrument that includes a housing having an active electrical connector and a return electrical connector configured to operably engage a distal end of an electrosurgical instrument shaft. The housing encapsulates an elongated return electrode and a pair of insulative tubes configured to house a wire-like active electrode. The elongated return electrode includes a clevis at a distal end thereof and operably engages to the return electrical connector at a proximal end thereof. The wire-like active electrode operably engages at one end thereof to the active electrical connector. A donut-like insulator operably engages to the clevis of the elongated return electrode, the donut-like ceramic insulator configured to support the wire-like active electrode therearound. A tensioning mechanism is configured to operably engage an opposite end of the wire-like active electrode and tension the wire-like active electrode about the donut-like insulator during assembly.

In aspects according to the present disclosure, the tensioning mechanism includes at least one bolt, at least one nut and at least one washer, the at least one washer configured to crimp the wire-like active electrode against the at least one respective nut to vary the tensioning of the wire-like active electrode during assembly. In other aspects according to the present disclosure, the at least one washer is at least one of a spring washer or a wave washer.

In aspects according to the present disclosure, the proximal end of the return electrode is threadably engaged to the return electrical connector. In other aspects according to the present disclosure, the donut-like insulator is secured to the clevis of the elongated return electrode by a rivet. In yet other aspects according to the present disclosure, the donut-like insulator includes a groove defined therein configured to seat the wire-like active electrode as the wire-like active electrode transitions therearound. In aspects according to the present disclosure, the active electrical connector operably secures to the housing via a square-shaped nut.

Provided in accordance with aspects of the present disclosure is an electrode assembly for an electrosurgical instrument that includes a housing configured to operably receive a distal end of an electrosurgical instrument shaft. The housing includes a pair of apertures defined on opposite sides thereof. The housing encapsulates an insulative core sandwiched between a pair of return electrodes, the insulative core including a slot defined about a periphery thereof configured to at least partially receive a wire-like active electrode. The wire-like active electrode is configured to connect at both ends thereof to an active electrical connector operably engaged to the housing and the pair of return electrodes is configured to connect to a return electrical connector operably engaged to the housing. The active and return electrical connectors are adapted to connect to opposite polarities of an electrosurgical generator. A tensioning mechanism is configured to tension the active electrode about the insulative core during assembly. The tensioning mechanism including a C-shaped clip having a central web supporting a pair of resilient arms on either end thereof. The arms each including a finger projecting inwardly therefrom, the fingers of the C-shaped clip are configured to be received within the apertures defined in the housing upon engagement of the C-shaped clip on the housing. The fingers cooperate to engage the wire-like active electrode on opposite ends thereof to tension the wire-like active electrode about the insulative core.

In aspects according to the present disclosure, the fingers include an anti-slip material disposed thereon. In other aspects according to the present disclosure, the active electrical connector and the return electrical connector are concentrically disposed within a single electrical connector. In yet other aspects according to the present disclosure, the C-shaped clip includes an aperture defined therein configured to receive the single electrical connector.

In aspects according to the present disclosure, the tension of the C-shaped clip is variable depending on the length of at least one the fingers. In other aspects according to the present disclosure, the tension of the C-shaped clip is variable depending on the resiliency of at least one of the arms.

In aspects according to the present disclosure, the wire-like active electrode is housed in an insulative tube on one side of the insulative core. In aspects according to the present disclosure, at least a portion of the active electrode remains exposed to treat tissue when seated within the slot defined in the insulative core.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIGS. 7A-7D are various views of another embodiment of an end effector assembly in accordance with the present disclosure;

DETAILED DESCRIPTION

Figure 1:
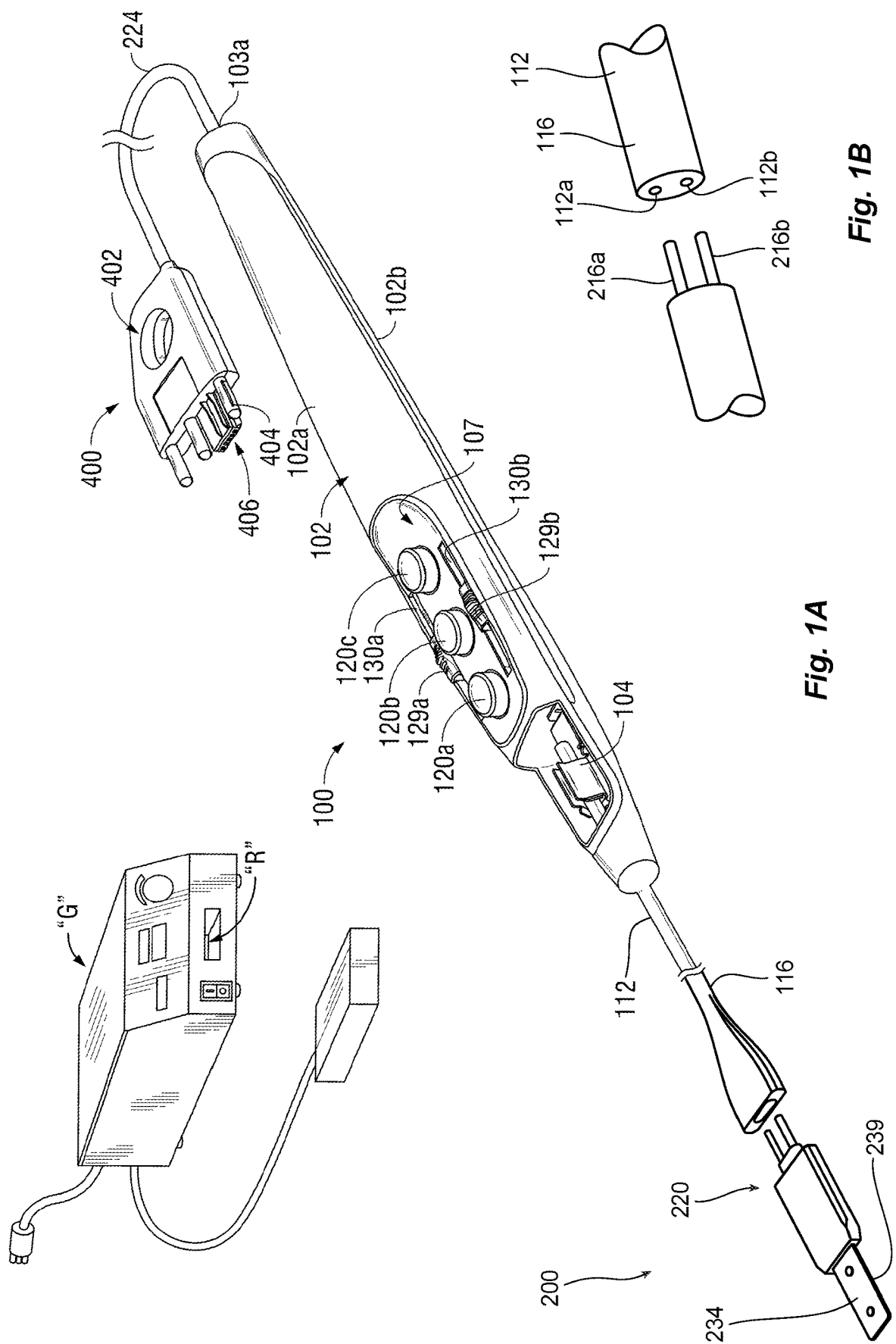
FIG. 1A is a perspective view of an electrosurgical system including an electrosurgical pencil including a housing having a shaft extending therefrom with an end effector attached to a distal end thereof, the end effector configured for bipolar resection in accordance with an embodiment of the present disclosure.
FIG. 1B is a greatly enlarged view of a proximal end of the end effector and the distal end of the shaft of the electrosurgical pencil housing.

Particular embodiments of the presently disclosed electrosurgical pencil configured for bipolar resection are described in detail with reference to the drawing figures wherein like reference numerals identify similar or identical elements. As used herein, the term "distal" refers to that portion which is further from the user while the term "proximal" refers to that portion which is closer to the user or clinician. The term "leading edge" refers to the most forward edge with respect to the direction of travel while the term "trailing edge" refers to the edge opposite the leading edge with respect to the direction of travel.

FIGS. 1A-1B sets forth a perspective view of an electrosurgical system including an electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. Pat. No. 7,156,842 to Sartor et al.

Figure 2:
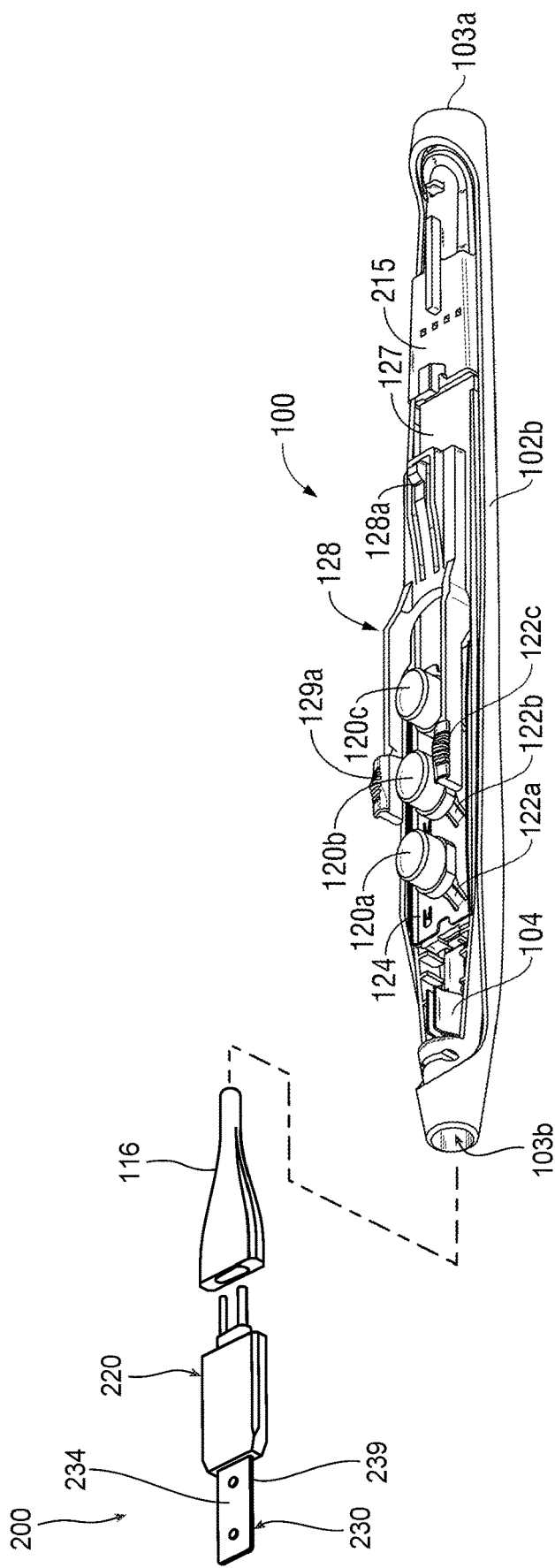
FIG. 2 is a front, top perspective view of the electrosurgical pencil of FIG. 1, with a top-half shell of the housing removed.

As seen in FIGS. 1A, 1B and 2, electrosurgical pencil 100 includes an elongated housing 102 having a top-half shell portion 102a and a bottom-half shell portion 102b. The elongated housing 102 includes a distal opening 103b, through which a shaft 112 extends, and a proximal opening 103a, through which connecting wire 224 (see FIG. 1A) extends. Top-half shell portion 102a and bottom-half shell portion 102b may be bonded together using any suitable method, e.g., sonic energy, adhesives, snap-fit assemblies, etc.

Electrosurgical pencil 100 further includes a shaft receptacle 104 disposed at a distal end 103b of housing 102 that is configured to receive the shaft 112 of a selectively removable end effector assembly 200. Electrode assembly 200 is configured to electrically connect to generator "G" through various electrical conductors (not shown) formed in the shaft 112, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 112 is selectively retained by shaft receptacle 104 disposed in housing 102. Shaft 112 may include a plurality of conductive traces or wires along the length of the shaft 112. The conductive traces or wires may be fabricated from a conductive type material, such as, for example, stainless steel, or shaft may be coated with an electrically conductive material. Shaft receptacle 104 is fabricated from electrically conductive materials or includes electrically conductive contacts configured to couple with the plurality of conductive traces or wires of the shaft 112. Shaft receptacle 104 is electrically connected to voltage divider network 127 (FIGS. 2 and 4) as explained in more detail below. Conductive traces or wires of the shaft electrically connect to the electrode assembly as explained in more detail below.

As seen in FIG. 1A, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

Electrosurgical pencil 100 includes at least one activation switch, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112.

More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. Pat. No. 7,503,917 to Sartor et al.

Figure 3:
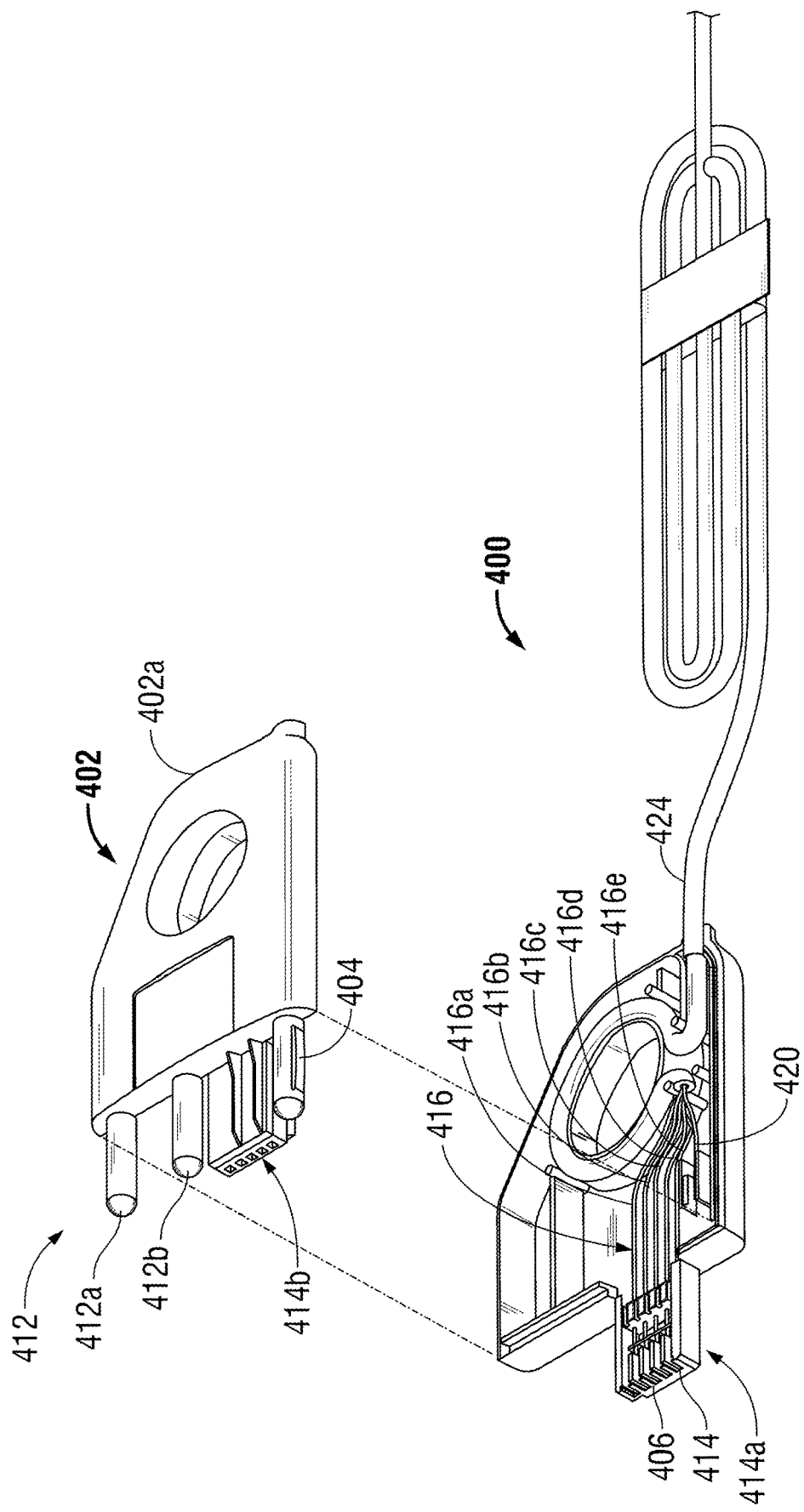
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect.

Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

Figure 7A:
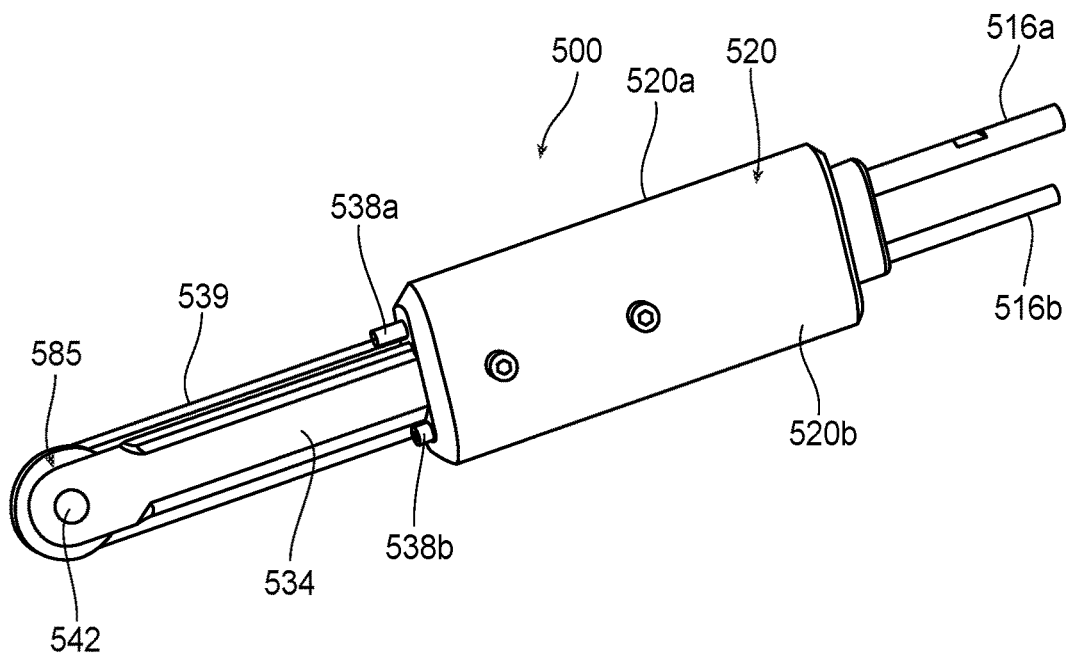

As seen in FIG. 3, fourth and fifth wires (e.g., first RF line 416d and second RF line 416e) are provided and electrically connect to respective active and return electrodes 239, 234 respectively, of the end effector assembly 200 (or end effector assembly 300, 500 as explained in more detail below with respect to FIGS. 7A-8). Since first RF line 416d and second RF line 416e are directly connected to the end effector assembly 200 first RF line 416d and second RF line 416e bypass the VDN 127 and are isolated from VDN 127 and control wires 416a-416c. By directly connecting the first RF line 416d and second RF line 416e to the end effector assembly 200 (or end effector assembly 300, 500 as explained in more detail below) and isolating the VDN 127 from the RF energy transmission, the electrosurgical current does not flow through VDN 127. This in turn, increases the longevity and life of VDN 127 and/or activation switches 120a, 120b, 120c.

Figure 4:
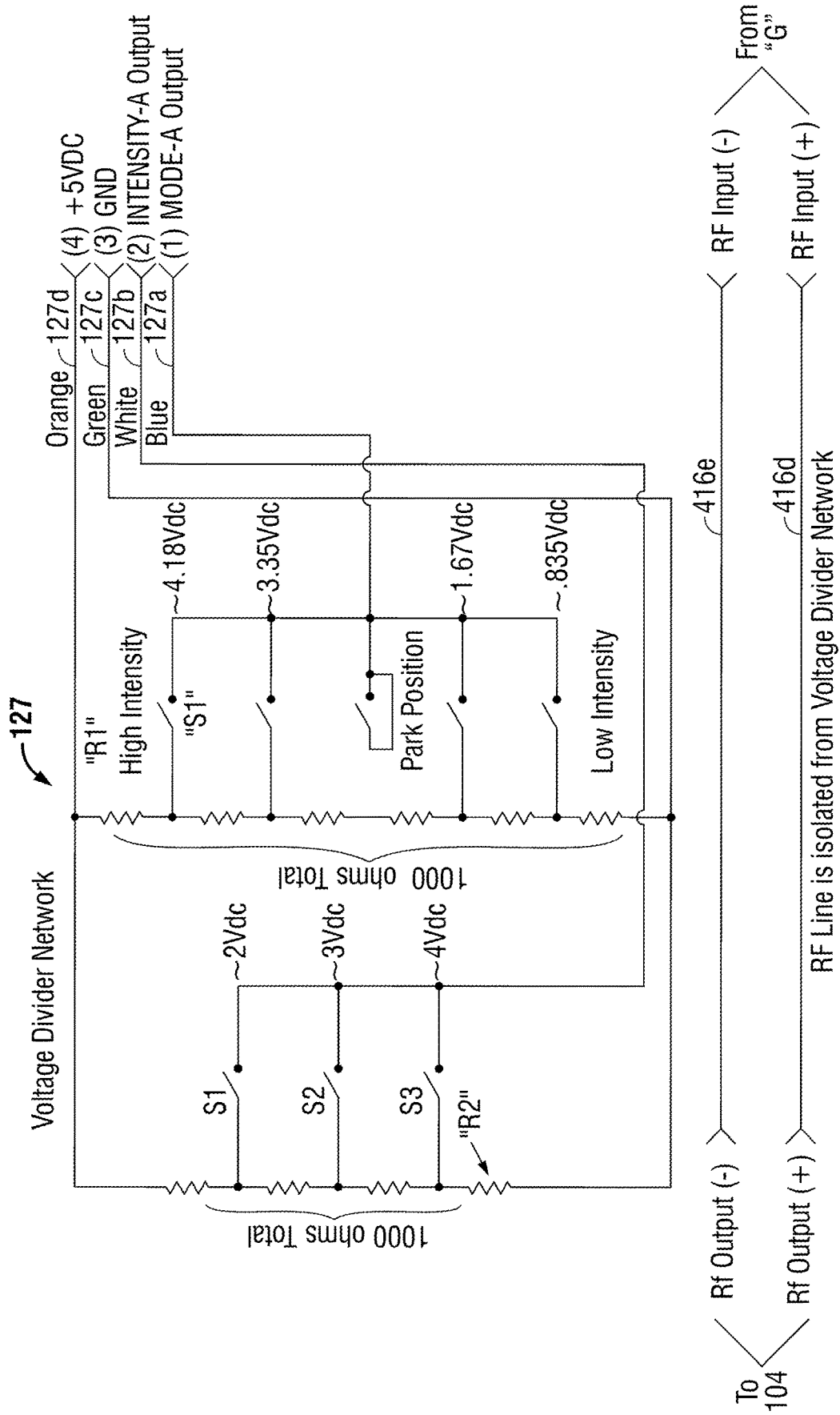
FIG. 4 is a schematic illustration of the voltage divider network of the present disclosure.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the active electrode and return electrodes of the end effector assembly 200 (or end effector assembly 300, 500 as explained in more detail below).

By way of example only, VDN 127 may include a plurality of resistors "R1" (e.g., six resistors), connected in a first series between third transmission line 127*c* and fourth transmission line 127*d*. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127*a* of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of end effector assembly 200 (or end effector assembly 300) and the arrangement of the active and return electrodes 239, 234. The selection of the end effector assembly 200 (or end effector assembly 300, 500), the intensity setting, and duty cycle determines the surgical effect. The settings may be selected manually by the user or automatically. For example, the electrosurgical generator "G" may automatically determine the type of end effector assembly 200 (or end effector assembly 300, 500) and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402*a* and a second half-section 402*b* operatively engageable with one another, e.g., via a snap-fit engagement. First half-section 402*a* and second half-section 402*b* are configured and adapted to retain a common power pin 404 and a plurality of electrical contacts 406 therebetween.

Common power pin 404 of plug assembly 400 extends distally from housing portion 402 at a location between first half-section 402*a* and second half-section 402*b*. Common power pin 404 may be positioned to be off center, i.e., closer to one side edge of housing portion 402 than the other. Plug assembly 400 further includes at least one a pair of position pins 412 also extending from housing portion 402. Position pins 412 may be positioned between the first half-section 402*a* and the second half-section 402*b* of housing portion 402 and are oriented in the same direction as common power pin 404.

A first position pin 412*a* is positioned in close proximity to a center of housing portion 402 and a second position pin 412*b* is positioned to be off center and in close proximity to an opposite side edge of housing portion 402 as compared to common power pin 404. First position pin 412*a*, second position pin 412*b* and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414*a* extending from second half-section 402*b* of housing portion 402 and a cover portion 414*b* extending from first half-section 402*a* of housing portion 402. In this manner, when the first half-section 402*a* and the second half-section 402*b* are joined to one another, cover portion 414*b* of prong 414 encloses the body portion 414*a*. Prong 414 may be positioned between common power pin 404 and first position pin 412*a*. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1A).

Since prong 414 extends from second half-section 402*b* of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416*a*-416*c* electrically connected to a respective electrical contact 406, and first RF line 416*d* and second RF line 416*e* electrically connected to a respective electrical contact 406.

Figure 5:
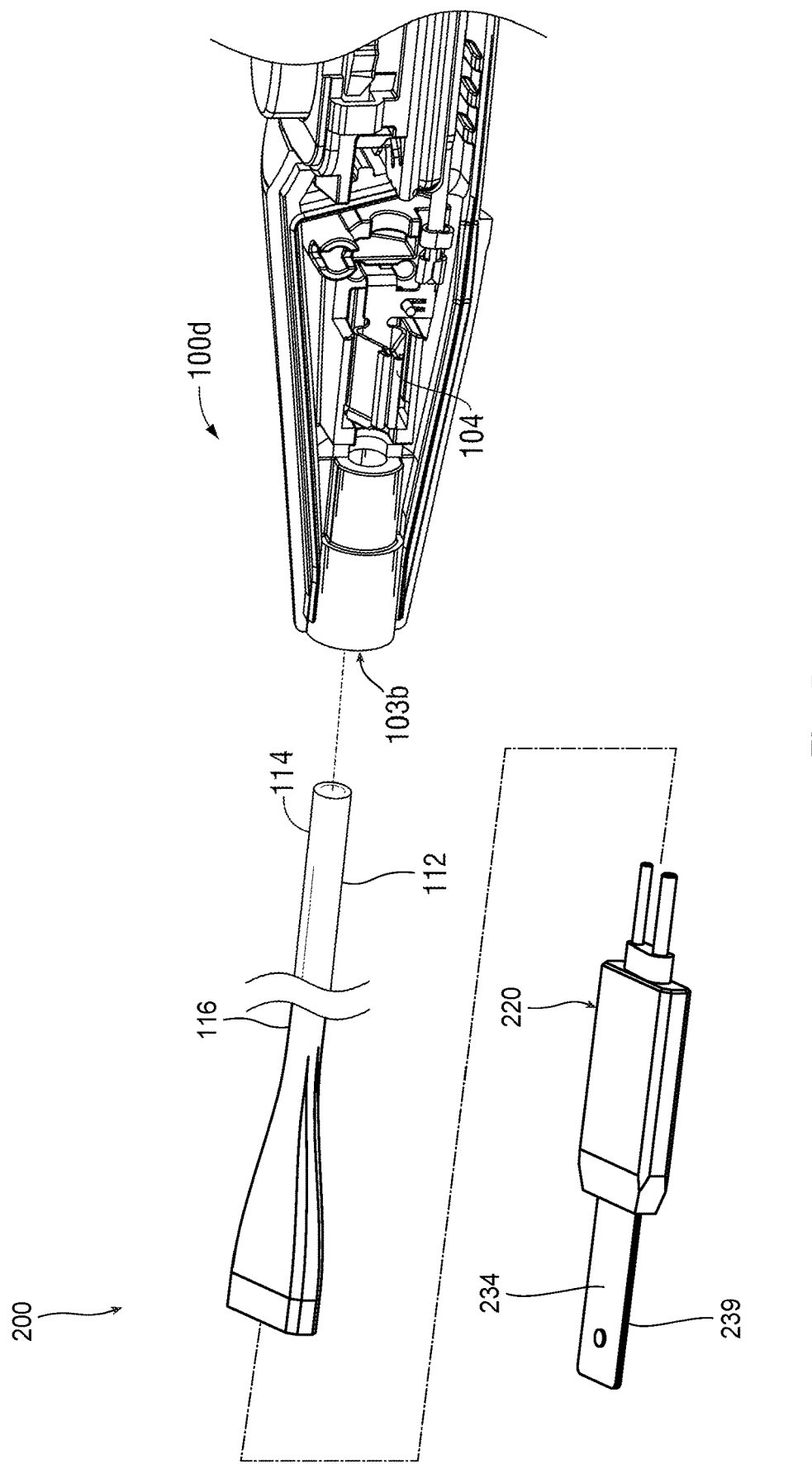
FIG. 5 is a partial, cross-sectional view of an end effector assembly of an electrosurgical pencil, in accordance with an embodiment of the present disclosure.

Turning now to FIG. 5, the end effector assembly 200 of electrosurgical pencil 100 is shown wherein a proximal portion 114 of shaft 112 is configured to mechanically and electrically engage shaft receptacle 104. Shaft 112 and shaft receptacle 104 are configured to provide a plurality of suitable electrical connections therebetween to facilitate the delivery of electrosurgical energy from the electrosurgical generator "G" (See FIG. 1) to the active 239 and return electrode 234 of the end effector assembly 200 (or active electrode 339 and return electrode 334 of FIG. 8 or active electrode 539 and return electrode 534 of FIGS. 7A-7D explained in further detail with below).

At least a portion of the shaft 112 is inserted into distal opening 103b of the elongated housing 102 to engage shaft receptacle 104. Shaft receptacle 104 is configured to mechanically and electrically couple the shaft 112 to the elongated housing 102. Electrical connections may include one or more electrical connectors (or electrical connector pairs) that connect to the active and return electrodes 239 and 234. Shaft 112 and shaft receptacle 104 may include a locking device, such as, for example, a shaft locking pin that slides into and engages a shaft locking pin receptacle (not explicitly shown). Any suitable securing and/or locking apparatus may be used to releasably secure the shaft 112 to the elongated housing 102. As described herein, the shaft 112 is interchangeable with the elongated housing 102. In other embodiments, shaft 112 is integrated into the elongated housing 102 and is not replaceable.

Turning back to FIG. 1B, a proximal end of the end effector assembly 200 includes a pair of electrical connectors 216a, 216b that is configured to electromechanically couple to a distal end 116 of shaft 112. More particularly, electrical connectors 216a, 216b are configured to mechanically engage respective slots 112a, 112b defined within a distal end of shaft 112. In this manner, the end effector assembly 200 may be interchangeable with shaft 112 and shaft receptacle 104 without having to redesign the interchangeable mechanical connection of the shaft 112 with the shaft receptacle 104 of the electrosurgical pencil 100. Alternatively, shaft receptacle 104 may be designed to selectively accommodate connectors 216a, 216b to provide the proper electrical polarity to end effector assembly 200 upon engagement thereof.

Figure 6A:
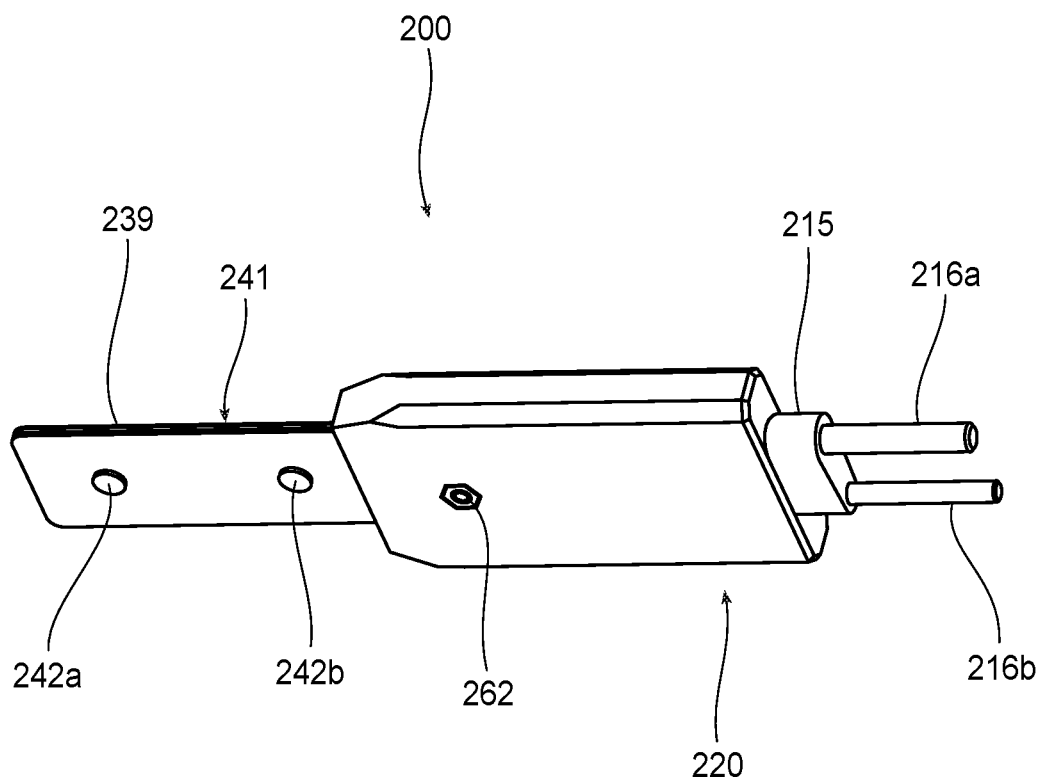
FIG. 6A is an enlarged, top, perspective view of the end effector assembly of the present disclosure.
Figure 6B:
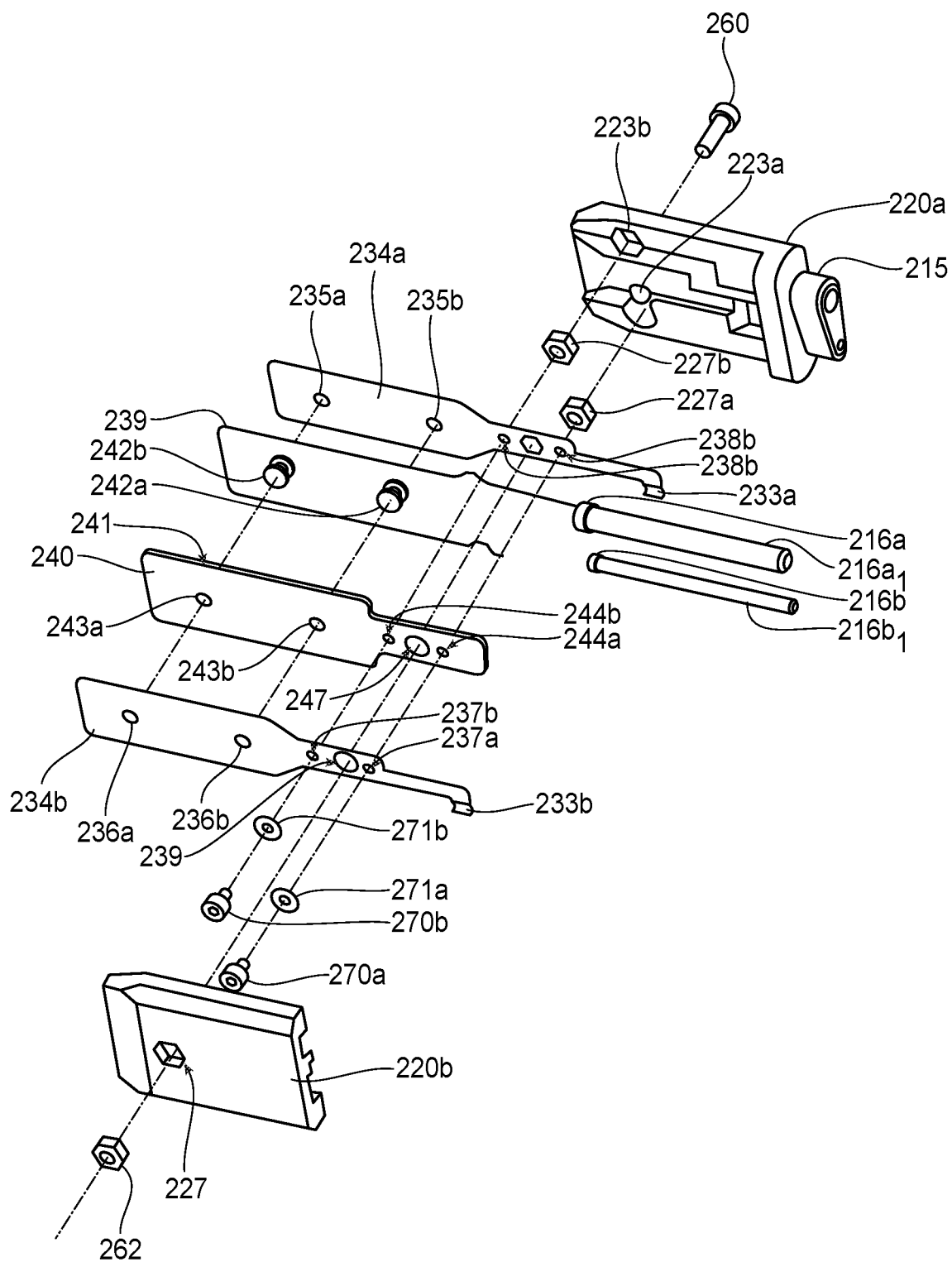
FIG. 6B is an enlarged, top, exploded view of the end effector assembly of FIG. 6A.

FIGS. 6A-6B show various views of one embodiment of the end effector assembly 200 for use with the electrosurgical pencil 100. End effector assembly 200 includes a housing 220 that is configured to mechanically and electrically couple to a distal end 116 of shaft 112. Housing 220 includes two housing halves 220a, 220b that cooperate to encase electrodes 234a, 234b and an active electrode or cutting wire 239. The housing halves 220a, 220b may be ultrasonically welded together or mechanically engaged in some other fashion, e.g., snap-fit, adhesive, etc. As mentioned above, the distal end 116 of shaft 112 includes a pair of slots 112a, 112b that is configured to mechanical engage proximal connectors 216a, 216b, which, in turn, mechanically and electrically couple to electrodes 234a, 234b and wire 239.

The pair of housing halves 220a, 220b encapsulate the return electrodes 234a, 234b, an insulative core 240 and the respective distal ends 216a1, 216b1 of the connectors 216a, 216b. Housing halves 220a, 220b are secured via screw 260 and nut 262. Nut 262 may be recessed within a nut cavity 227 defined within an outer facing side of housing half 220b. Screw 260 may be recessed within housing half 220a. More particularly, each return electrode 234a, 234b affixes to a respective opposing side of the insulative core 240 and is held in place via a pair of rivets 242a, 242b. Each rivet 242a, 242b engages a corresponding aperture defined in the insulative core 240 (namely, apertures 243a, 243b) and each electrode 234a (namely, apertures 235a, 235b), 234b (namely, apertures 236a, 236b). The insulative core 240 may be made from any insulative material, e.g., ceramic, and is dimensioned slightly larger than the dimensions of respective return electrodes 234a, 234b.

Respective proximal ends 233a, 233b of each return electrode 234a, 234b is configured to electrically engage connector 216b. Proximal ends 233a, 233b may include geometry to facilitate connection to the connector 216b, e.g., an arcuate flange or other mechanical interface.

Wire 239 is configured to partially seat within a slot 241 defined along the outer peripheral edge of insulative core 240. Part of the wire 239 remains exposed to allow electrically cutting (as explained in more detail below). Wire 239 is configured to electrically connect to connector 216a (e.g., active electrode) which supplies a cutting current when the electrosurgical pencil 100 is activated. Wire 239 may be made from tungsten or any other type of material commonly used in the art.

Figure 6C:
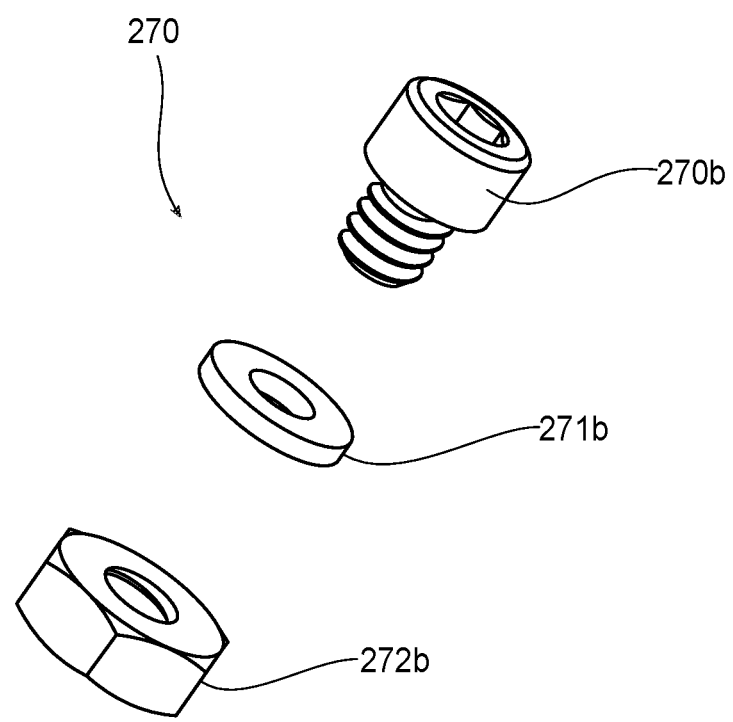
FIG. 6C is a greatly enlarged, exploded view of a tensioning mechanism for use with the end effector assembly according to the present disclosure.

During assembly and once wire 239 is seated within slot 241, the wire 239 is tensioned utilizing a tensioning mechanism 270. Tensioning mechanism 270 includes a pair of bolts 270a, 270b, a corresponding pair of washers 271a, 271b and a corresponding pair of nuts 272a, 272b (See FIG. 6C). Wire 239 is fed from connector 216a, between bolt 270a and nut 272a pair, and atop washer 271a and then around the distal-most edge of the insulative core 240 to be secured between bolt 270b and nut 272b pair atop washer 271b. Each washer 271a, 271b crimps the wire 239 to the face of the respective nut 272a, 272b. Various types of washers 271a, 271b may be used to facilitate this purpose, e.g., spring washers or wave washers. Pinching the wire 239 against the nuts 272a, 272b via the washers 271a, 271b provides tension to the wire 239 and secures the wire 239 within the slot 241. During assembly and testing, the bolts 270a, 270b may be tightened as necessary to provide a requisite amount of tension to wire 239. The addition of a washer 271a, 271b provides consistent and robust tensioning that may be modified as necessary for testing and final assembly.

Each bolt 270a, 270b engages a corresponding aperture defined in the core 240 (namely, apertures 244a, 244b) and each electrode 234a (namely, apertures 237a, 237b), 234b (namely, apertures 238a, 238b). Nuts 272a, 272b may be seated within respective nut cavities 223a, 223b defined within housing half 220a.

Once assembled, end effector assembly 200 may be selectively attached to the distal end 116 of the shaft 112 as explained above. A proximal end of the housing 220 (once assembled) may include a proximal housing support 215 that engages and supports the connectors 216a and 216b. Proximal housing support 215 may be tapered to facilitate assembly and orientation of the end effector assembly 200 with the shaft 112 or pencil housing 102.

As mentioned above, the wire 239 may be made from any suitable conductive material such as tungsten, surgical stainless steel, etc. Tungsten is particularly favored since various geometries for the wire 239 may be easily 3D printed providing additional robustness over traditional wire designs while offering an optimized surface area to increase cutting efficiency. Moreover, a sheet including a plurality of tungsten wires 239 may be 3D printed to facilitate the manufacturing process. Moreover, multiple geometries may be easily integrated with the mating geometry of the various mechanical interfaces staying the same. The exposed edge (not explicitly shown) of wire 239 is configured for cutting and is designed to concentrate electrosurgical energy to increase cutting efficiency.

The return electrodes 234a, 234b are made from a conductive material and insulated from the wire 239 via the insulative core 240. As mentioned above, the insulative core 240 may be made from a material that provides good thermal and non-conductive properties. Each return electrode 234a, 234b provides a return path for the electrosurgical energy from the wire 239 such that the circuit is completed.

Turning now to FIGS. 7A-7D, another embodiment of an end effector assembly is shown and designated end effector assembly 500. End effector 500 is a double-sided treatment or cutting tool inasmuch as the active electrode 539 is exposed on both sides (or top and bottom) of the end effector assembly 500. FIG. 8 discussed below discloses a single-sided version of an end effector assembly 300.

End effector assembly 500 is similar to the end effector assembly 200 described above and, as such, only those details necessary for a complete understanding of end effector assembly 500 are discussed herein. End effector 500 includes a housing 520 including housing halves 520a, 520b that cooperate to encapsulate the active electrode 539, return electrode (ground plate) 534 and the tensioning mechanism 570. One or more bolt and nut arrangements 560a, 560b may be utilized to secure the two housing halves 520a, 520b together.

Figure 7B:
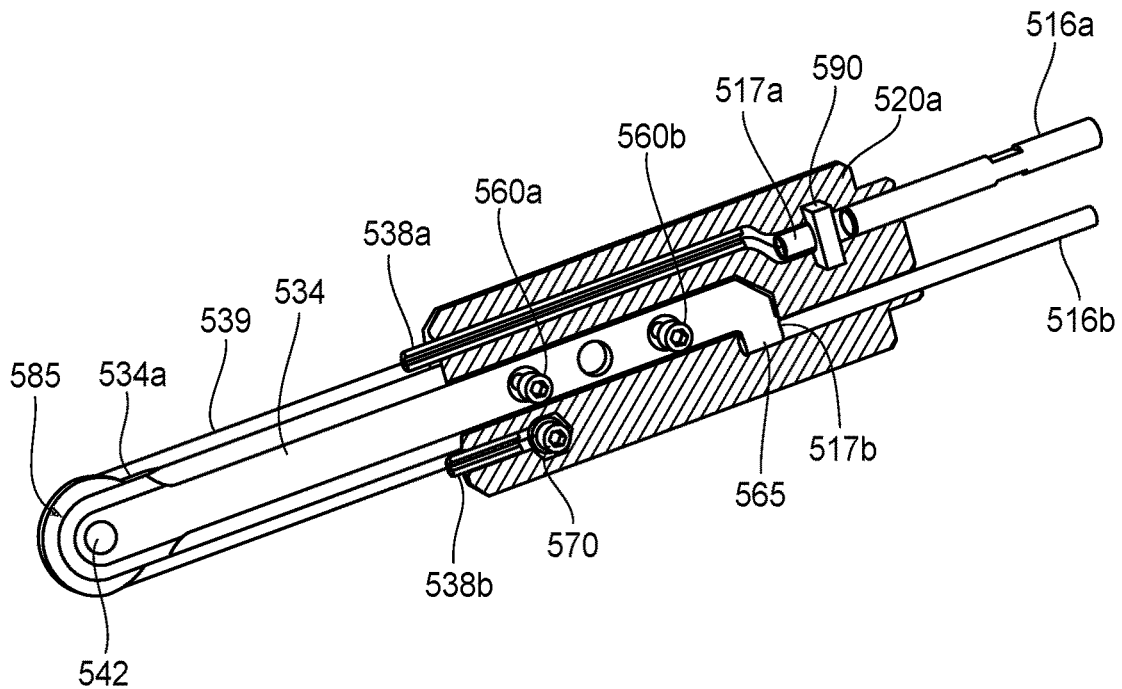

End effector 500 includes a donut-style tip 585 configured to guide active electrode (or wire) 539 therearound for engagement with the tensioning mechanism 570. Tensioning mechanism 570 is similar to the tensioning mechanism 270 described above. Donut-style tip 585 may be made from ceramic or any other type of durable material that both electrically isolates the active electrode 539 from the return electrode (ground plate) 534 and provides the necessary rigidity to support the active electrode 539 for tissue treatment (e.g., cutting). As shown in FIGS. 7B-7D, return electrode (ground plate) 534 includes a clevis at a distal end thereof configured to support the donut-style tip 585 thereon. Tip 585 includes a rivet hole 586 disposed therethrough configured to support a rivet 542 therein for mounting the tip 585 to the return electrode (ground plate) 534. Tip 585 also includes a groove 589 defined therearound configured to securely seat the active electrode 539 therein.

Donut-style tip 585 guides the active electrode 539 therearound to transition the active electrode 539 distally to proximally to permit the active electrode 539 to treat tissue (e.g., cut tissue) on either side of the return electrode (ground plate) 534. More particularly, and as best shown in FIG. 7B, active electrode 539 engages active electrical connector 516a at a distal end 517a thereof and is secured in place via nut 590. Nut 590 may be hexagonal as explained above or square to allow the nut 590 to securely seat against housing half 520a more effectively by reducing the number of sides associated with the nut 590.

Active electrode 539 is then fed from active electrical connector 516a through a hypotube 538a, to and around donut-style tip 585 seated within groove 589, to a second hypotube 538b and into engagement with the tensioning mechanism 570. As explained in detail above, tensioning mechanism 570 provides the necessary tension onto active electrode 539 to ensure effective tissue treatment (e.g., cutting). The donut-style tip 585 provides the necessary rigidity and electrical isolation of the active electrode 539 at the distal end of the end effector assembly 500 to ensure tissue treatment (e.g., cutting).

Return electrode (ground plate) 534 is supported on the housing 520 by bolt and nut arrangements 560a, 560b as well as connected to the return electrical connection 516b by a threaded connection 565 disposed at a proximal end of the return electrode (ground plate) 534. Distal end 517b of the return electrical connector 516b is threaded to engage the corresponding threaded connection 565 disposed in the proximal end of the return electrode (ground plate) 534.

Return electrode (ground plate) 534 and rivet 542 provide a large, robust surface area of electrical return for the active electrode 539 when engaging tissue to facilitate bipolar treatment thereof In addition, the size of the return electrode (ground plate) 534 provides better heat capability to the end effector assembly 500 which reduces the chances of eschar buildup. Further, the donut-style tip 585 is keyed (e.g., riveted) to the robust ground plate 534 to provide stability at the distal end of the end effector assembly 500 and to prevent shifting thereof during use.

Figure 8:
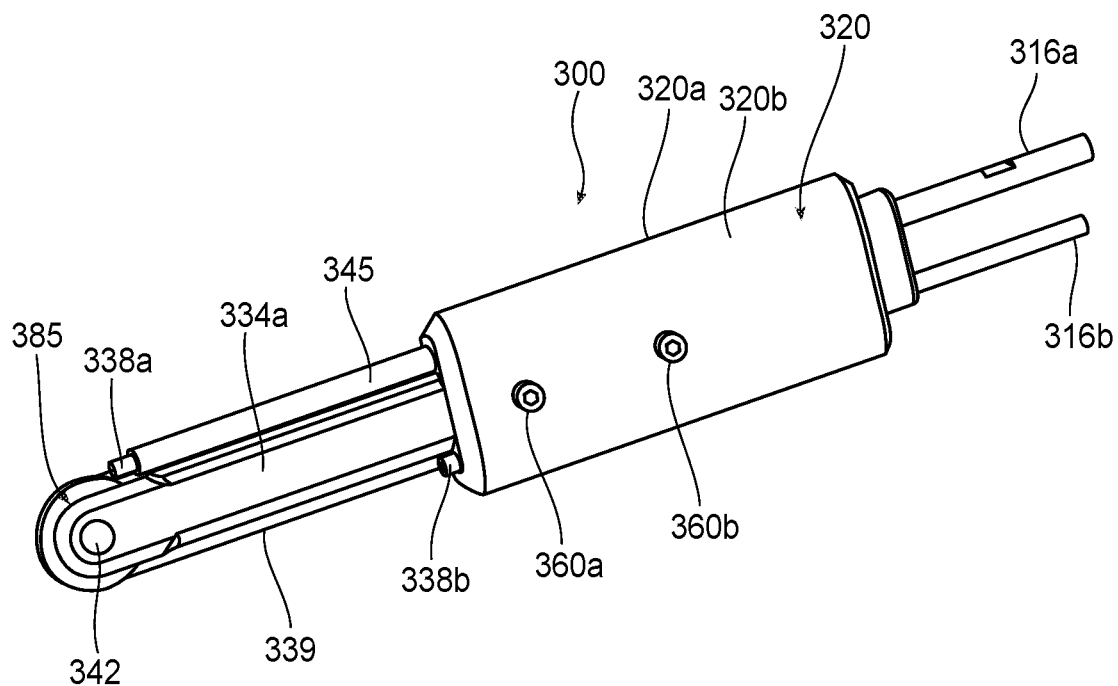
FIG. 8 is a top perspective view of another embodiment of an end effector assembly in accordance with the present disclosure.

Turning now to FIG. 8, another embodiment of an end effector assembly is shown and designated end effector assembly 300. This end effector assembly 300 is particularly suited for single-sided tissue treatment or cutting as explained in more detail below.

End effector assembly 300 is similar to the end effector assembly 200 described above and, as such, only those details necessary for a complete understanding of end effector assembly 300 are discussed herein. End effector assembly 300 includes a housing 320 made up of two housing halves 320a, 320b that are configured to encapsulate both an active electrode 339 and a return electrode (ground plate) 334 similar to end effector assemblies 200 and 500 described above. One or more bolt and nut arrangements 360a, 360b may be utilized to secure the two housing halves 320a, 320b together.

End effector 300 includes a donut-style tip 385 configured to guide active electrode (or an active wire) therearound for engagement with a tensioning mechanism (not shown but see FIGS. 7B-7D). Donut-style tip 385 may be made from ceramic or any other type of durable material that both electrically isolates the active electrode 339 from the ground electrode (ground plate) 334 and provides the necessary robustness and rigidity to support the active electrode 339 for tissue treatment (e.g., cutting). Tip 385 includes a rivet hole (not shown) disposed therethrough configured to support a rivet 342 therein for mounting the tip 385 to the return electrode (ground plate) 334.

End effector 300 includes many of the same features as described above with respect to end effector assemblies 200 and 500 and, as such, only the differences are described herein. More particularly, active electrode 339 is fed from active electrical connector 316a through a hypotube 338a, to and around donut style tip 385 seated within a groove (not shown), to a second hypotube 338b and into engagement with the tensioning mechanism (not shown). As explained in detail above, the tensioning mechanism provides the necessary tension onto active electrode 339 to insure effective tissue treatment (e.g., cutting). The donut-style tip 385 provides the necessary rigidity and electrical isolation of the active electrode 339 at the distal end of the end effector assembly 300 to ensure tissue treatment (e.g., cutting).

Hypotube 338a extends to a point proximate the donut-style tip 385 to insure electrical isolation of the active electrode 339 from the return electrode (ground plate) 334. An electrically conductive tube 345 is affixed to the return electrode 334 and encapsulates the hypotube 338a and active electrode 339. Tube 345 acts as a return path in conjunction with return electrode (ground plate) 334 and insures one-side tissue treatment.

Return electrode (ground plate) 334 is supported on the housing 320 by bolt and nut arrangements 360a, 360b as well as connected to the return electrical connector 316b in a similar manner as described above with respect to end effector assemblies 200 and 500.

Figure 9:
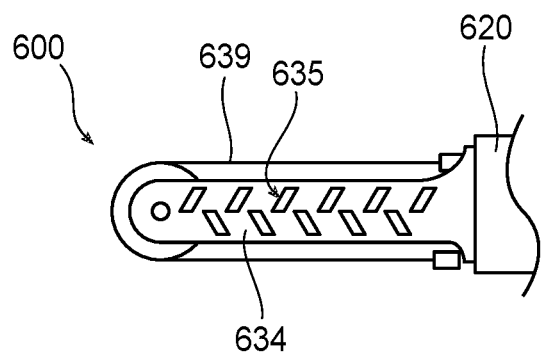
FIG. 9 is a side view of another embodiment of an end effector assembly in accordance with the present disclosure.

FIG. 9 shows another embodiment of an end effector assembly, namely, end effector 600. End effector assembly 600 is similar to the end effector assemblies 200, 300 and 500 described above and, as such, only those details necessary for a complete understanding of end effector assembly 600 are discussed herein. End effector assembly 600 includes a housing 620 that is configured to encapsulate both an active electrode 639 and a return electrode (ground plate) 634. Return electrode (ground plate) 634 includes a series of venting slots 635 defined therein configured to dissipate heat while still maximizing the surface area for electrical return during activation. Any arrangement of venting slots 635 is envisioned to accomplish this purposes, e.g., alternating slots, staggered slots, variously-sized slots, etc.

Figure 10A:
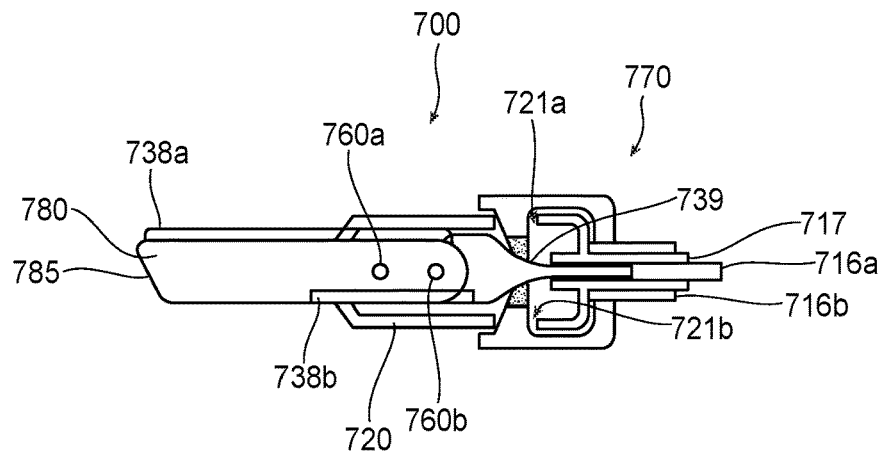
FIGS. 10A-10C are various views of an end effector assembly including a tensioning mechanism for use with any of the disclosed end effector assemblies disclosed herein.
Figure 10B:
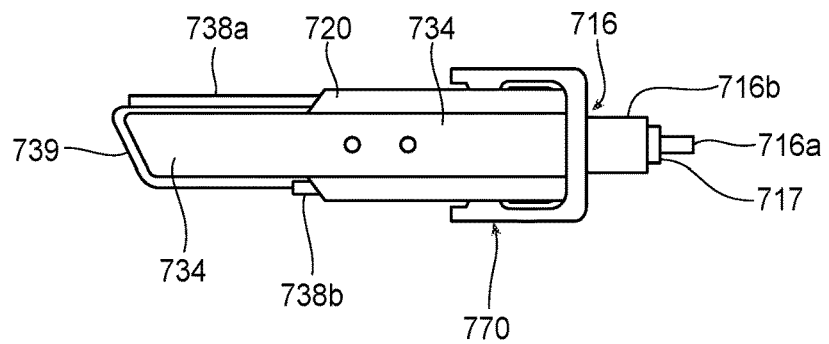
Figure 10C:
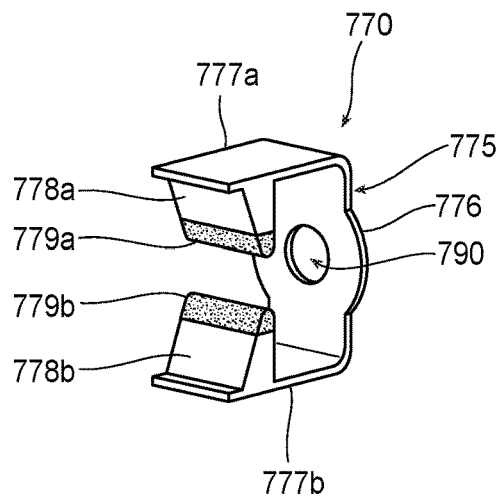

FIGS. 10A-10C show another embodiment of a tensioning mechanism 770 for use with end effector assembly 700 or any of the above described end effector assemblies or versions thereof. End effector assembly 700 includes a housing 720 made up of two housing halves (not shown) that are configured to encapsulate both an active electrode 739 and a return electrode (ground plate) 734 similar to end effector 200 described above. One or more bolt and nut arrangements 760a, 760b may be utilized to secure the two housing halves together. A ceramic insulator (or ceramic blade) 780 supports the return electrode (ground plate) 734 on either side thereof along the length of the end effector assembly 700.

In this embodiment, an active electrical lead 716a and a return electrical lead 716b are concentrically disposed within a single electrical connector 716 that selectively attaches to a pencil 100 similar to the manner described above. Active electrode 739 securely engages active electrical lead 716a disposed in the center of connector 716 and return electrode 734 securely engages return electrical lead 716b concentrically disposed about the active lead 716a. An insulator 717 separates the electrical leads 716a, 716b.

Active electrode 739 is fed from active electrical lead 716a through a hypotube 738a, to and around a tip 785 of the ceramic insulator 780 seated within a groove (not shown), to a second hypotube 738b and back into engagement with active electrical lead 716a. Return electrical lead 716b operably engages the return electrode (ground plate) 734 which extends on either side of the ceramic insulator (blade) 780. Return electrode (ground plate) 734 provides a robust surface area for an electrical return path during activation.

Tensioning mechanism 770 includes a C-shaped clip 775 configured to operably engage the housing 720 on either side thereof. C-shaped clip 775 includes a web 776 having upper and lower arms 777a, 777b, respectively, that extend therefrom. Each arm 777a, 777b includes a respective finger 778a, 778b that inwardly extends from a distal end thereof in mutual opposition relative to one another to form the C-shaped clip 775. Arms 777a, 777b are resiliently biased toward one another. Fingers 778a, 778b include a friction-based or anti-slip material 779a, 779b disposed on respective distal ends thereof configured to frictionally grip or secure the active electrode 739.

Housing 720 includes apertures 721a, 721b disposed on either side thereof that are configured to operably receive the respective inwardly extending fingers 778a, 778b of clip 775 therein. The resilient bias of arms 777a, 777b secure and maintain the clip 775 atop the housing 720 once engaged.

Once the active electrode 739 is engaged around the end effector assembly 700 and tip 785 and secured at both ends to the active electrical lead 716a, the clip 775 is engaged atop the housing 720. Clip 775 includes an aperture 790 defined therein configured to allow clip 775 to slide atop single electrical connector 716 (FIG. 10B). As can be appreciated, clip 775 is mounted atop single electrical connector 716 during an assembly step.

Upon engagement and as best seen in FIG. 10A, the distal ends of the fingers 778a, 778b pinch the active electrode 739 on either end thereof to provide additional tension thereon. The friction-based or anti-slip material 779a, 779b on the distal ends of the respective fingers 778a, 778b maintain tension on the active electrode 739 on either side thereof. The resilient bias of the arms 777a, 777b may be customized to provide different amounts of tension depending upon a particular purpose. This may be accomplished by varying the length of one or both fingers 778a, 778b during molding of C-shaped clip 775, or varying the resiliency of one or both arms 777a, 777b.

As explained in detail above, the tensioning mechanism 770 provides the necessary tension onto active electrode 739 to ensure effective tissue treatment (e.g., cutting). More particularly, the clip 775, and the tensioning bias associated therewith, tightly controls the amount of tension on the active electrode 739 eliminating concerns associated with shorting (too little tension) and wire fatigue (too much tension).

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be affected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An electrode assembly for an electrosurgical instrument, comprising:
    a housing including an active electrical connector and a return electrical connector configured to operably engage a distal end of an electrosurgical instrument shaft, the housing encapsulating an elongated return electrode and a pair of insulative tubes configured to house an active electrode, the elongated return electrode having a distal end including a clevis and a proximal end operably engaged to the return electrical connector, the active electrode being operably engaged at one end to the active electrical connector;
    an insulator operably engaged to the clevis of the elongated return electrode, the insulator configured to support the active electrode; and
    a tensioning mechanism configured to operably engage an opposite end of the active electrode and tension the active electrode about the insulator during assembly.

2. The electrode assembly of claim 1, wherein the tensioning mechanism includes at least one bolt, at least one nut and at least one washer, the at least one washer configured to crimp the active electrode against the at least one respective nut to vary the tensioning of the active electrode during assembly.

3. The electrode assembly of claim 2, wherein the at least one washer is at least one of a spring washer or a wave washer.

4. The electrode assembly of claim 1, wherein the proximal end of the return electrode is threadably engaged to the return electrical connector.

5. The electrode assembly of claim 1, wherein the insulator is secured to the clevis of the elongated return electrode by a rivet.

6. The electrode assembly of claim 1, wherein the insulator includes a groove configured to seat the active electrode.

7. The electrode assembly of claim 1, wherein the active electrical connector operably secures to the housing via a square-shaped nut.

8. An electrode assembly for an electrosurgical instrument, comprising:
    a housing;
    an active electrical connector extending from a proximal end of the housing;
    a return electrical connector extending from the proximal end of the housing and configured to couple to an electrosurgical instrument;
    a return electrode having a distal end portion extending distally from the housing and a proximal end portion disposed within the housing and coupled to the return electrical connector;
    an active electrode having a first end and a second end opposite the first end, the first end of the active electrode coupled to the active electrical connector;
    an insulator coupled to the distal end portion of the return electrode, the insulator configured to support the active electrode; and
    a tensioning mechanism disposed within the housing and coupled to the second end of the active electrode, the tensioning mechanism configured to tension the active electrode.

9. The electrode assembly of claim 8, wherein the tensioning mechanism includes a nut and a washer, the washer configured to crimp the active electrode against the nut to vary the tensioning of the active electrode.

10. The electrode assembly of claim 8, wherein the proximal end portion of the return electrode is threadably coupled to the return electrical connector.

11. The electrode assembly of claim 8, wherein the distal end portion of the return electrode includes a clevis coupled to the insulator.

12. The electrode assembly of claim 11, wherein the insulator is coupled to the clevis of the return electrode by a rivet.

13. The electrode assembly of claim 8, wherein the insulator includes a groove configured to seat the active electrode.

14. The electrode assembly of claim 8, wherein the active electrical connector is secured to the housing via a square-shaped nut.

15. An electrode assembly for an electrosurgical instrument, comprising:
    a housing;
    an active electrical connector extending from a proximal end of the housing;
    a return electrical connector extending from the proximal end of the housing;
    a return electrode having a distal end portion extending distally from the housing and a proximal end portion disposed within the housing and coupled to the return electrical connector;
    an active electrode coupled to the active electrical connector;
    an insulator disposed at the distal end portion of the return electrode, the insulator configured to support the active electrode; and
    a tensioning mechanism disposed within the housing and configured to tension the active electrode.

16. The electrode assembly of claim 15, wherein the active electrode has a first end coupled to the active electrical connector and a second end, opposite the first end, coupled to the tensioning mechanism.

17. The electrode assembly of claim 15, wherein the tensioning mechanism includes a nut and a washer, the washer configured to crimp the active electrode against the nut to vary the tensioning of the active electrode.

18. The electrode assembly of claim 15, wherein the proximal end portion of the return electrode is threadably coupled to the return electrical connector.

19. The electrode assembly of claim 15, wherein the distal end portion of the return electrode includes a clevis coupled to the insulator.

20. The electrode assembly of claim 19, wherein the insulator is coupled to the clevis of the return electrode by a rivet.

* * * * *